United States Patent [19]
Douvas et al.

[11] 3,990,453
[45] Nov. 9, 1976

[54] APPARATUS FOR CATARACT SURGERY

[76] Inventors: Nicholas G. Douvas, 4200 N. Gratiot, Port Huron, Mich. 48060; Henry T. Dinkelkamp, 200 W. Orchard Place, Mount Prospect, Ill. 60056

[22] Filed: Feb. 28, 1975

[21] Appl. No.: 554,161

Related U.S. Application Data

[63] Continuation-in-part of Ser. No. 354,376, April 25, 1973, Pat. No. 3,882,872.

[52] U.S. Cl. ............................... 128/305; 30/123.3; 30/174
[51] Int. Cl.² ...................... A61F 9/00; A61B 17/32
[58] Field of Search ............ 30/123.3, 174; 128/305

[56] References Cited
UNITED STATES PATENTS

| | | | |
|---|---|---|---|
| 2,462,701 | 2/1949 | Wirth | 30/123.3 |
| 2,492,158 | 12/1949 | Compte et al. | 30/174 X |
| 2,818,852 | 1/1958 | Kugler | 128/305 X |
| 3,732,858 | 5/1973 | Banko | 128/305 X |

FOREIGN PATENTS OR APPLICATIONS 591,548  8/1947  United Kingdom ................ 128/305

*Primary Examiner*—Channing L. Pace
*Attorney, Agent, or Firm*—Harness, Dickey & Pierce

[57] ABSTRACT

A cutting tip for a rotary motor-driven cutting instrument for cataract surgery consists of a hollow stationary tube and a tubular cutter journaled therein and projecting therefrom, the cutting tip being open at its end and having concentric axially directed arcuate cutting edge portions. An annular passage extends between the concentric tubes, and the stationary tube has an orifice in the side close to the tip. An irrigating fluid is adapted to be discharged through the side opening of the stationary tube, and a suction connection to the internal tube is effective to remove severed tissue through the hollow rotatable internal cutter.

5 Claims, 10 Drawing Figures

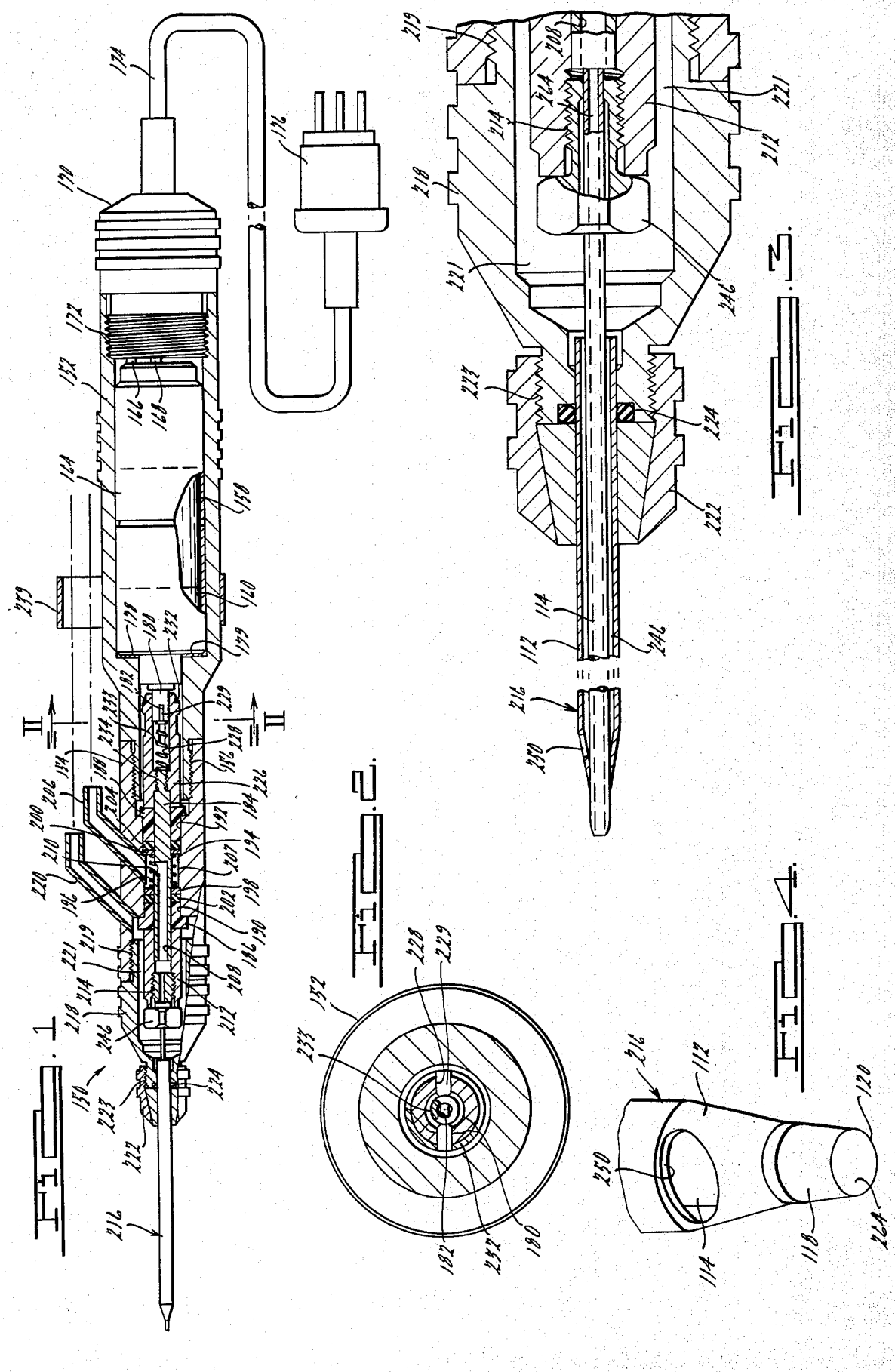

3,990,453

APPARATUS FOR CATARACT SURGERY

CROSS REFERENCE TO RELATED APPLICATION

The present application is a continuation in part of United States Patent application Ser. No. 354,376, filed Apr. 25, 1973, now U.S. Pat. No. 3,882,872, granted May 13, 1975, entitled "Method and Apparatus For Cataract Surgery."

BACKGROUND OF THE INVENTION

The instruments disclosed in the above-mentioned patent application Ser. No. 354,376 include cutting tips having a generally cylindrical configuration with a combined cutting edge and suction orifice at the side of the tip adjacent the end and which are effective for certain operative procedures where the tip of the instrument is moved laterally to remove the cataractous tissue. In order to core and fragment some such tissue prior to the use of one of the side cutters, improved end cutting tips disclosed in said prior application are provided, which the surgeon may use initially to speed the operative procedure, and with substantial benefit to the patient.

In line with the above, the object of the present invention is to provide for an instrument of the character described an improved cutting tip which is adapted to core fragment tissue to assist in the separation and removal thereof.

A related object is to provide such an improved tip of the end cutting type which is constructed similarly to and is quickly interchangeable with side cutting tips of the types disclosed in the aforementioned prior application.

Other objects and advantages will become apparent upon consideration of the present disclosure in its entirety.

BRIEF DESCRIPTION OF THE FIGURES OF DRAWING

FIG. 1 is a substantially diametric longitudinal sectional view of a surgical instrument equipped with a cutting tip constructed in accordance with the present invention, some of the parts being shown in elevation;

FIG. 2 is a cross section taken substantially on the line II—II of FIG. 1 and looking in the direction of the arrow;

FIG. 3 is an enlarged longitudinal sectional view of the cutting tip, showing adjacent parts somewhat diagrammatically;

FIG. 4 is a perspective view of the end of the cutting tip, on a further enlarged scale;

DETAILED DESCRIPTION OF PREFERRED FORM OF THE INVENTION

Figure 5:
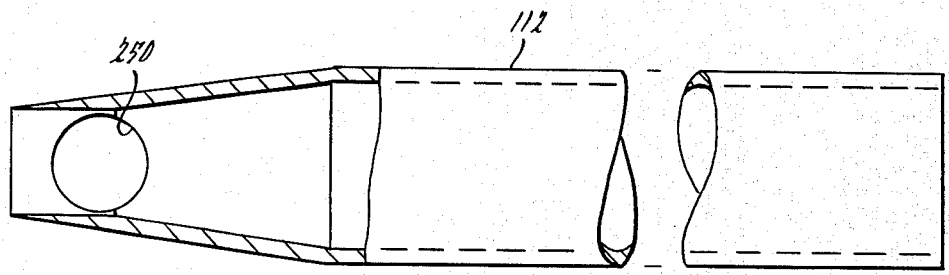
FIG. 5 is a view of the stator, partly in side elevation and partly in diametric longitudinal section, on a greatly enlarged scale and centrally broken away.
Figure 6:
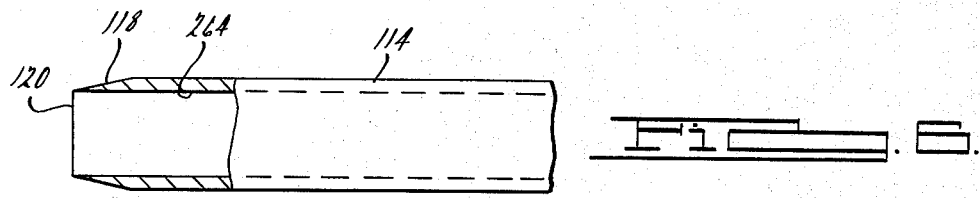
FIG. 6 is a similar view of the outer end of the rotor.

As disclosed in FIG. 1 the cutting instrument or probe generally designated 150 comprises a generally tubular motor housing 152 and a generally tubular spindle body 154 threaded onto the forward end of housing 152 as at 156. A 12-volt DC permanent magnet motor 158 is contained within housing 152, and a gear head 160 is mounted onto the axially forward end of motor 158. The forward end of motor 158 is telescopically inserted into the open rear end of the gear head housing. A tubular shell 164 is telescopically inserted over the rear end of motor 158 to enclose the terminal connector construction via which electricity is conducted to motor 158. A pair of spring-loaded electrical terminals 166, 168 extend through the rear of shell 164 and are biased into engagement with suitable electrical connections in an end plug 170 which is threaded into the open rear end of housing 152 as at 172. A cable 174 containing positive, negative and ground wires leads from plug 170 to a three-terminal connector 176 which is adapted to be connected to a source of 12-volt DC power for energizing motor 158. The diametrically reduced forward end of gear head 160 fits within a correspondingly diametrically-reduced forward portion of the bore of housing 152. An annular anti-slip disk 178 is fitted over this diametrically-reduced portion of gear head 160. The annular forwardly facing shoulder of gear head 160 bears against the shoulder 179 within the bore of housing 152 through anti-slip disk 178. The axial force with which gear head 160 bears against shoulder 179 is determined by the compression of the springs associated with terminals 166, 168 when end plug 170 is threaded onto body 152. The frictional contact provided by disk 178 between gear head 160 and shoulder 179 prevents motor 158 from angularly slipping within the bore of housing 152 when motor torque is developed. A drive shaft 180 having an open diametrical slot 182 at the forward end thereof protrudes from the diametrically reduced forward portion of gear head 160. When electric power is applied via connector 176 through terminals 166, 168 to motor 158, shaft 180 rotates. The speed of shaft 180 is equal to the speed of motor 158 divided by the gear ratio of gear head 160. Gear reduction of 6.3 to 1 and 11.8 to 1 have been found to provide suitable ranges of cutting speeds when used in conjunction with motor 158 having a maximum speed of 11,000 rpm. (Without a gear head up to 11,000 rpm can be obtained.) It will be appreciated that the optimum cutting speed will depend upon the cutter tip construction and the nature of the surgery. The speed may be varied according to well-known techniques by varying the percentage of voltage applied to the motor.

A drive shaft 184 is journaled for rotation within spindle body 154 via a pair of axially spaced glass filled Teflon bearings 186 and 188. The rear end of shaft 184 is operatively coupled for rotation with shaft 180 via an axial lost motion coupling which will be explained later in greater detail. Bearings 186 and 188 are inserted into opposite ends of diametrically reduced bore segments 190, 192 which are separated by a further diametrically reduced bore segment 194. A coil spring 196 is disposed around the portion of shaft 184 within bore portion 194. Spring 196 bears against washers 198 and 200 which are arranged within bore segments 190 and 192 respectively so that washer 198 compresses an annular seal 202 between itself and bearing 186 and washer 200 compresses an annular seal 204 between itself and bearing 188 to thereby seal the ends of bore segment 194. Bearings 186 and 188 are retained axially in the illustrated position with the respective lips bearing against shoulders at the ends of bore segments 190 and 192. Retention is effected by means of a tubular adapter body 212 which is inserted over and affixed to the end of shaft 184 which protrudes forwardly through bearing 186, and a tubular coupling 226 which is threaded onto the rear end of shaft 184 as at 234. Coupling 226 is threaded onto shaft 184 an amount sufficient to draw adapter 212 against bearing 186 and itself (i.e., coupling 226) against bearing 188 whereby adapter body 212 and coupling 226 retain bearings 186 and 188 in the illustrated position.

A tubular conduit 206 is inserted into an inclined bore in the side wall of body 154 to intercept bore segment 194. A passage 208 extends rearwardly through shaft 184 from the forward end thereof and terminates at a hole 210 in the side wall of shaft 184. Hole 210 opens to the axially sealed annular space 207 around shaft 184 within bore segment 194. The adapter 246 of a cutting tip assembly 216 is threaded onto the forward end of adapter body 212 as at 214. Thus a passage is provided from tube 206 through space 207, hole 210, passage 208 and coupling 226 to adapter 212. As will be seen in greater detail hereinafter, aspirating suction is applied to this passage and thence through tip 216 to the cutting area thereof.

An end cap 218 is threaded onto the forward end of spindle body 154 as at 219. Cap 218 and the forward end of body 154 are arranged relative to adapter body 212 such that an axially extending free space 221 is provided around adapter body 212 within the instrument. An inlet tube 220 is inserted into an inclined bore in body 154 to intercept space 221. As will be seen in greater detail hereinafter, irrigating fluid is introduced via tube 220, through space 221 and a passage in tip assembly 216 for dispensing irrigating fluid onto the surgical area. The portion of tip assembly 216 forward of adapter 246 extends through the bore of end cap 218 and the tip assembly is retained by means of a collet and nut 222 which is inserted over the forward end of tip assembly 216 and threaded onto the forward end of end cap 218 as at 223. An O-ring gasket 224 seals the bore of end cap 218 around tip 216. A clip 239 for retaining flexible conduits to tubes 206 and 220 is provided around housing 152.

The coupling arrangement between shaft 180 and shaft 184 provides an axial lost motion connection whereby axial forces from shaft 180 are not transmitted through to the cutting tip 216, and the motor and gear head can be readily assembled and replaced if necessary. Details of this coupling can be seen in FIGS. 1 and 2. A pair of diametrically opposed axial slots 228 in coupling 226 extend forwardly from the rear end thereof. A key 229 extends diametrically across the rear end of coupling 226 with the ends of key 229 received in slots 228. The key is suitably shaped so that it cannot be substantially displaced radially of the coupling. An annular retaining ring 232 around coupling 226 axially retains key 229 in slots 228. A coupling spring 233 is disposed within coupling 226 and bears against the rear end of shaft 184 and the central portion of key 229 thereby biasing key 229 axially rearwardly against ring 232. When end plug 170 is being threaded onto spindle body 154, the motor and gear head are urged axially forwardly so that shaft 180 fits into the bore of coupling 226 and slot 182 engages the central portion of key 229. This provides an axial lost motion connection with key 229 being displaced axially forwardly of coupling 226 against the bias of spring 233 an amount sufficient to accommodate the motor and gear head. Furthermore in the assembled instrument any axial loading on shaft 184 by shaft 180 is cushioned by spring 233.

The details of cutting tip assemmbly 216 are illustrated in FIGS. 3, 4, 5 and 6. Cutting tip assembly 216 represents one form of tip which may be used with instruments such as shown herein and in said prior patent application. The assembly 216 comprises a tubular stator 112 and a rotary cutter generally designated 114. The stator is sealed with respect to the instrument by the O-ring 224, as noted above, and is open at its rear end into the chamber 221. The rotary cutter, which is an uninterrupted tube, continues therethrough and has a fluid-tight mechanical connection to coupling body 212. The O.D. of the rotor is less than the I.D. of the stator so that an annular axially extending fluid passage 246 is provided between the stator and rotor tubes. One or more discharge openings 250 are provided in tube 112 at the forward end thereof. As illustrated the openings may be of circular shape and may face generally radially outwardly. The irrigating fluid which enters instrument 150 via tube 220 flows through space 221, into the rear end of stator 112, along passage 246 and out via openings 250 onto the surgical area. The rear end of rotor 114 is welded in the bore in adapter 246. The bore 264 of rotor 114 is thereby open to passage 208. Aspirating suction which enters instrument 150 via tube 206 is transmitted through passage 208, and bore 264, to the open forward end of the rotor tip. With suction applied to tube 206 excess irrigating fluid as well as cut tissue pieces can be sucked through the open end of rotor 114, along bore 264 and passage 208 back for discharge via tube 206. When motor 158 is energized, the rotation of shaft 180 is transmitted via coupling 226, shaft 184 and adapter body 212 to turn adapter 246 and hence rotor 114. The stator is constrained against rotation by collet nut 222.

Referring to FIG. 4, the open forward end of inner tube 114 projects beyond the end of the stator and is honed around the outside to a generally conical shape which tapers radially inwardly in the forward direction as at 118 so that tube 114 has a razor-sharp cutting edge 120 lying substantially on a circle in a plane perpendicular to the axis of tip 216. Aspiration is effected through the bore 264 of inner tube 114, as noted.

Figure 7:
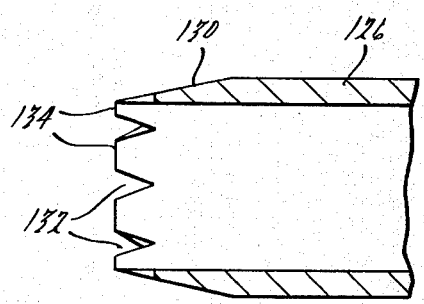
Figure 9:
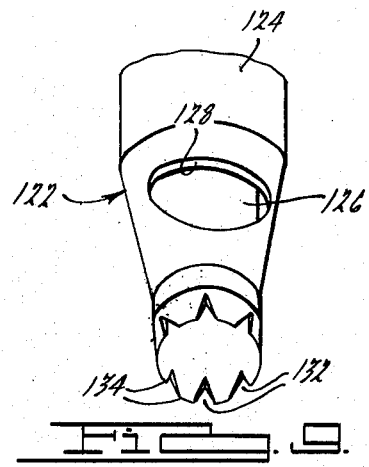
FIG. 9 is a perspective view of the tip end portion of the rotor of FIG. 7.

A second "end-core" cutting tip 122, shown in FIGS. 7 and 9, is of generally similar construction having outer and inner tubular portions 124 and 126 respectively corresponding to portions 112, 114 and a discharge opening 128 for the irrigating fluid passage between the inner and outer tubes. Aspiration is via the bore of inner tube 126. The projecting forward end of inner tube 126 is also open ended and conically honed as at 130, but a plurality of circumferentially spaced axial serrations 132 are provided around the forward end of the tube. Thus, the cutting edge of tube 126 is not circumferentially continuous as was edge 120 of tip portion 114, but rather inner tube 126 has a plurality of individual arcuate razor-sharp cutting edges 134 lying substantially on a circle perpendicular to the tip axis.

Figure 8:
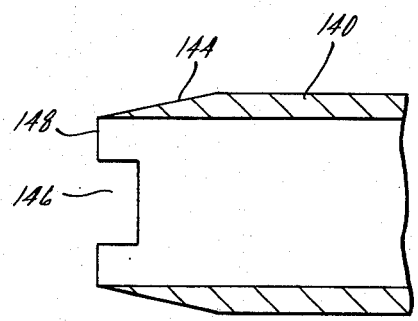
FIGS. 7 and 8 are views similar to FIG. 6 showing modified forms of rotor cutting tip ends.
Figure 10:
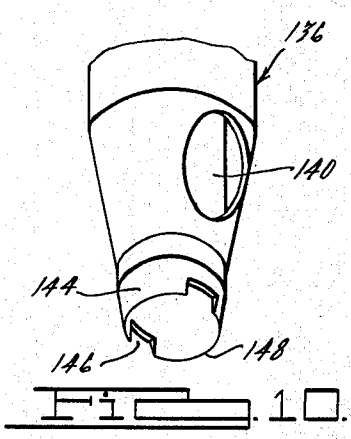
FIG. 10 is a view similar to FIG. 9 of the tip end portion of the rotor of FIG. 8.

A third "end-core" cutting tip 136 shown in FIGS. 8 and 10 is of generally similar construction and the open forward end of inner tube 140 is also externally conically honed as at 144. A pair of diametrically opposed rectangular slots 146, extend axially rearwardly from the forward end of tube 140. In this way tube 140, which in other respects corresponds to inner tubes 114, 126 previously described, has a pair of diametrically opposed, arcuately extending, razor-sharp cutting edges 148 lying substantially on a circle perpendicular to the tip axis. Aspiration is via the bore of inner tube 140 as in the other embodiments hereof.

As mentioned before, the particular advantage of the "end-core" type cutting tip resides in its coring and fragmenting capability. With the "end-core" tip of the present invention such coring and fragmenting is greatly facilitated and represents a notable improvement in surgical procedures. Thus by virtue of the present invention, calcified or fibrous plaques of lens opacity can be fragmented, and aspirated as can dense, rigid, congenital posterior polar cataract, membranous traumatic-after-cataract and senile brunescent nuclear cataract. The cutting tips herein disclosed do not possess the shearing type cutting action of the side cutting tips described in the aforementioned parent patent application Ser. No. 354,376; rather tip portions 216, 124 and 136 exhibit cutting action, which results in fragmentation and coring of tissue, when the rotating rotor is pressed slightly into the tissue axially. Cutting can be done with or without simultaneous aspiration and irrigation according to the desire of the surgeon performing the procedure. By intially using any of the "end-core" tips in a surgical procedure, larger masses of tissue can be efficiently broken apart and sucked up by the cutting instrument. As a result the invention can provide improved efficiency by reducing overall surgical time, while simultaneously, because of its improved cutting action, minimizing or eliminating the risk of injury to adjacent tissue which is not intended to be removed.

This Detailed Description of Preferred Forms of the Invention, and the accompanying drawings, have been furnished in compliance with the statutory requirement to set forth the best mode contemplated by the inventors of carrying out the invention. The prior portions consisting of the "Abstract of the Disclosure" and the "Background of the Invention" are furnished without prejudice to comply with administrative requirements of the Patent Office.

What is claimed is:

1. An axially extending cutting tip assembly for fragmenting and coring tissue during cataract surgery comprising in combination with a supporting handle portion and an outer stator tube fixed with relation to the handle portion, an inner rotor tube rotatable about its longitudinal axis within said stator tube and projecting axially through and from a constricted and closely fitted free forward end of said stator tube, said rotor tube having a free projecting end outside the stator tube and having a sharp cutting edge at said projecting end defining a circle perpendicular to the axis of the tube.

2. The cutting tip of claim 1 wherein said cutting edge is continuous.

3. The cutting tip of claim 1 wherein said cutting edge is discontinuous.

4. The cutting tip of claim 3 wherein said cutting edge comprises a pair of diametrically opposed arcuate segments separated by axial slots.

5. The cutting tip of claim 3 wherein said cutting edge comprises a plurality of arcuate segments lying entirely in a plane perpendicular to the axis of rotation and separated by axial serrations.

* * * * *